(12) United States Patent
Radcliffe et al.

(10) Patent No.: US 9,757,249 B2
(45) Date of Patent: *Sep. 12, 2017

(54) EXPANDABLE SPINAL IMPLANT

(71) Applicant: Amendia, Inc., Marietta, GA (US)

(72) Inventors: Jeffrey Scott Radcliffe, Marietta, GA (US); Joshua David Gunn, Woodstock, GA (US); Hansen A Yuan, Naples, FL (US)

(73) Assignee: Amendia, Inc., Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/473,180

(22) Filed: Mar. 29, 2017

(65) Prior Publication Data
US 2017/0202675 A1   Jul. 20, 2017

Related U.S. Application Data

(63) Continuation of application No. 14/259,760, filed on Apr. 23, 2014, now Pat. No. 9,642,720.

(60) Provisional application No. 61/918,395, filed on Dec. 19, 2013.

(51) Int. Cl.
*A61F 2/44*   (2006.01)
*A61F 2/46*   (2006.01)
*A61F 2/30*   (2006.01)

(52) U.S. Cl.
CPC .............. *A61F 2/447* (2013.01); *A61F 2/446* (2013.01); *A61F 2/4611* (2013.01); *A61F 2/4455* (2013.01); *A61F 2/4465* (2013.01); *A61F 2002/30507* (2013.01); *A61F 2002/30556* (2013.01); *A61F 2002/4475* (2013.01)

(58) Field of Classification Search
CPC ...... A61F 2/4465; A61F 2/446; A61F 2/4611; A61F 2002/30556; A61F 2002/30507; A61F 2002/30545; A61F 2002/30553; A61F 2002/30622; A61F 2002/30537; A61F 2002/30579; A61F 2002/3052; A61F 2002/30515; A61F 2002/3055; A61F 2002/4475
USPC ....................................................... 606/279
See application file for complete search history.

(56) References Cited

U.S. PATENT DOCUMENTS

| 5,658,335 | A  | 8/1997  | Allen |
| 6,176,882 | B1 | 1/2001  | Biedermann et al. |
| 6,733,535 | B2 | 5/2004  | Michelson |
| 7,850,733 | B2 | 12/2010 | Baynham et al. |
| 8,062,375 | B2 | 11/2011 | Glerum et al. |

(Continued)

*Primary Examiner* — Todd E Manahan
*Assistant Examiner* — Marcela I Shirsat
(74) *Attorney, Agent, or Firm* — David L. King

(57) ABSTRACT

An expandable implant device (100, 300, 600) for insertion between two vertebrae (400) is disclosed. The device (100, 300, 600) has a center body (10) one or more lift bodies (20, 40) and an external retaining band (60). The external retaining band (60) holds the sides (22, 42) of the one or more lift bodies (20, 40). The center body (10) has ramp surfaces (11) having a plurality or sets of ramps (11) sloped for allowing upward movement of the one or more lift bodies (20, 40). The sides (22, 42) have complimentary ramp surfaces that fit onto the ramps (11) of the center body (10). The height of the device (100, 300, 600) is increased by upward movement or downward movement or both of the one or more lift bodies (20, 40) driven by the lengthwise movement of the center body (10).

19 Claims, 14 Drawing Sheets

(56) References Cited

U.S. PATENT DOCUMENTS

| | | |
|---|---|---|
| 8,105,382 B2 | 1/2012 | Olmos |
| 8,398,713 B2 | 3/2013 | Weiman |
| 8,535,380 B2 | 9/2013 | Greenhalgh et al. |
| 9,642,720 B2 * | 5/2017 | Radcliffe et al. ..... A61F 2/4455 623/17.16 |
| 2010/0292796 A1 | 11/2010 | Greenhalgh et al. |
| 2011/0230965 A1 | 9/2011 | Schell et al. |
| 2013/0006361 A1 | 1/2013 | Glerum et al. |
| 2013/0085572 A1 | 4/2013 | Glerum et al. |
| 2013/0211526 A1 | 8/2013 | Alheidt et al. |

\* cited by examiner

EXPANDABLE SPINAL IMPLANT

RELATED APPLICATIONS

The present application is a continuation of co-pending application U.S. Ser. No. 14/259,760 filed on Apr. 23, 2014 entitled "Improved Expandable Spinal Implant".

TECHNICAL FIELD

The present invention relates to spinal implants generally, more particularly to an improved expandable spinal implant.

BACKGROUND OF THE INVENTION

Spinal stabilization can be achieved by providing an interbody implant. Some of these implants are bone, PEEK, solid titanium or similar non-bone implant material and some are hollow implants that provide for inclusion of a bone graft or other suitable material to facilitate bony union of the vertebrae.

Interbody implants can be inserted into the disc space through an anterior, posterior or lateral approach. In some systems, the implants are inserted into a bore formed between adjacent vertebral bodies in the cortical endplates and can extend into the cancellous bone deep to the cortical endplates. Implant size is typically selected such that the implants force the vertebrae apart to cause tensing of the vertebral annulus and other soft tissue structures surrounding the joint space. Tensing the soft tissues surrounding the joint space results in the vertebrae exerting compressive forces on the implant to maintain the implant in place.

It has been found desirable to keep the surgical opening as small as practical while still having sufficient room to insert the implant device and the end of an elongated tool or insertion instrument.

Advantageously, if the implant size could be reduced further that would allow the surgical opening to be reduced; however, once implanted the device needs to be expandable to provide sufficient spacing of the vertebrae.

A whole class of expandable interbody implant devices have been developed for this purpose. Some prior art devices use hydraulic expansion or inflatable balloons. Some devices are stackable elements piled on themselves to raise their height. Some use rotatable screw jack designs. Some are wedges that have a fixed hinged end and an opposite expandable end. All of the rotatable expandable devices using screw threads require the device to be round cylinders or posts.

One of the problems of such devices is the amount of post insertion manipulation required to reach a fully expanded properly space height is tedious and time consuming. Secondly, additional set screws or locking elements are often required to keep the device at its proper size. Thirdly, the devices of a circular shape are not the best fit for the adjacent vertebrae being spaced. Fourth, most of the devices have the internal space occupied with mechanisms limiting the amount of bone growth material available for packing the implants.

The wedge type implants generally contact the bone on an angle and expandable wedges when expanded simply expand on an angle not parallel to the vertebrae surface. This places localized high loading between the vertebrae because the wedge surfaces are not parallel to the vertebrae.

These and other limitations in the prior art have been corrected and solved by the present invention as disclosed herein.

SUMMARY OF THE INVENTION

An expandable implant device for insertion between two vertebrae has one or more lift bodies, preferably an upper lift body, a lower lift body and a center body. The center body is retractably moveable relative to a length of the device. The center body has a plurality of sloped ramps along opposing longitudinal extending sides. The upper body and lower body each have a plurality of complimentary sloped surfaces on sides adjacent to opposing sides of the center body. Upon lengthwise movement of the center body of the device, the one or more lift bodies move inward or outward relative to the center body, causing a retraction or expansion of height of the device. The device further has an exterior retaining band encircling the sides of the one or more lift bodies, upper and lower lift bodies. This retaining band prevents the sides of the one or more lift bodies to deflect and release from the ramp surfaces thereby sandwiching the sides of the lift bodies between the sides of the retaining band and the sides of the center body. The device further has a threaded fastener, the threaded fastener is a screw, having a rotatable fastener head retained at a distal trailing end of the retaining band by a clip affixed to a recess groove on the shank adjacent the head. The threaded fastener further has a threaded shank attached to a threaded opening at an end of the center body. Rotation of the rotatable fastener causes linear or lengthwise movement of the center body relative to the retaining band causing the one or more lift bodies to raise or lower. The retaining band further has a leading end having an opening. The leading end preferably is sloped having a conical or bullet nosed shape through which the opening is centered.

The sloped ramps are inclined directionally outward toward a leading end of the retaining band and rotation of the fastener device draws the center body toward the trailing end as the one or more upper or lower lift bodies or both move increasing the height of the device. In one embodiment employing two moveable lift bodies, the sloped ramps of the center body are formed preferably in the shape of a chevron, the chevrons having an apex at a midline of the center body. The apex directionally positioned closer to a trailing end and as the center body moves aft towards the trailing end, the complimentary surfaces of the lift bodies ride upwardly along the sloped ramps moving the lift bodies outwardly parallel to the midline increasing the height of the device. In embodiments having only one moveable lift body, the plurality of ramps can be an inclined straight line ramp.

The device further can have a nose portion at the leading end of the retaining band. The nose portion has a tapered head with a shank filling the opening of the leading end of the retaining band. The nose portion preferably has a central passageway extending along the shank through the tapered head to allow a guide wire to pass during implantation of the device. The tapered head of the nose portion preferably is conical or bullet shaped. In one embodiment, the shank is fixed to the center body and upon movement of the center body, the nose portion moves with the center body. When the nose portion is fully extended relative to the leading end of the retaining band the one or more lift bodies are retracted to a low height contracted position and the nose portion is retracted at least partially, if not completely, into the leading end opening of the retaining band when the lift bodies are fully expanded to a maximum height of the device. This feature shortens the overall length of the implant as the height is increased.

In another embodiment, the shank of the nose portion slip fits into an opening of the center body and the center body slides along the shank as it moves while the tapered head of the nose portion is larger than the opening abutting against the leading end of the retaining band as the shank of the nose portion is press fit into and is fixed to the leading end opening of the retaining band. This fixes the nose portion to the retaining band such that it is not moveable. When this embodiment is employed, the movement of the center body towards the aft end of the device causes the one or more lift portions to raise or lower as the center portion slides upon the shank of the nose portion.

When the device employs two moveable lift bodies, the upper lift body has a top surface or end and lower lift body has a bottom surface or end, the top end and bottom end each have an elongated opening extending from a respective upper and lower lift body. The center body is preferably formed as a hollow structure with sides forming an elongated opening communicating with the openings of the upper and lower lift bodies. Preferably, the center body has a pair of side openings and the retaining band has a complimentary set of side openings, one opening being at least partially aligned with each opening in the side of the center body. Each upper and lower lift body has a recessed cut out portion on each side. The recessed cut out portions form a lateral passageway open through the side openings in the center body, the cut out portions of the lift bodies and the side openings of the retaining band.

In the embodiments wherein only one lift body moves, the one moveable lift body will be as described above, but the bottom surface or end that is not moveable can be formed or attached as a base or a top of the retaining band. This can effectively eliminate one component. Preferably, this fixed base or top would have an opening and surface texture similar in appearance to the surface or end of the moveable lift body.

The threaded fastener preferably has a center opening or passageway for passing a guide wire through the device. This opening is aligned such that it will allow the guide wire to pass through the fastener and through the leading opening of the retaining band and through the nose portion opening such that the device can slide along the guide wire during implantation. When the center body is made as a hollow oblong or rectangular structure open at a top and a bottom the one or more lift bodies having aligned openings all forming a large cavity into which allograft bone filler can be inserted. When the retaining band formed as a hollow band, the sides of the one or more lift bodies are held between the sides of the center body and the retaining band along the length of the device. In one embodiment, the upper lift body has a top surface or end and the lower lift body has a bottom surface or end for abutting a pair of vertebrae such that upon implantation the expansion of the device increases the height of the device thereby spacing the vertebrae to the desired space as required. Each top end and each bottom end has an elongated opening. Each top end and each bottom end preferably has a gripping surface for abutting the vertebrae; this gripping surface can be a roughened surface and or a surface with a pattern to enhance bone growth formation along the abutting surfaces. Furthermore, the gripping surface can have a diamond shaped structure for allowing additional grip between the vertebrae. In the embodiment where only one lift body is moveable, the opposite top end or bottom end can be fixed to the retaining band with an appearance the same as the moveable end.

The lift bodies and center body are preferably made of metal or synthetic plastic. The device can be made of stainless steel or titanium or plastic or any combination thereof.

BRIEF DESCRIPTION OF THE DRAWINGS

The invention will be described by way of example and with reference to the accompanying drawings in which.

DETAILED DESCRIPTION OF THE INVENTION

Figure 1:
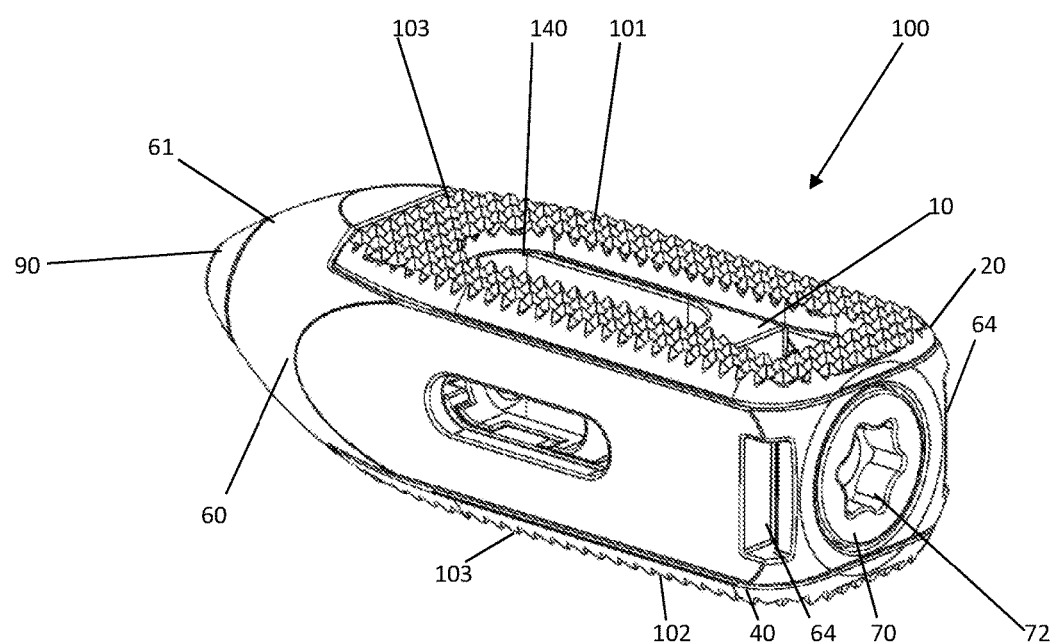
FIG. 1 is a perspective view of a first embodiment expandable implant device of the present invention.

With reference to FIGS. 1-4, a first embodiment device 100 is illustrated as made according to the present invention. As shown, the expandable implant device 100 in FIG. 1 is in the fully contracted and unexpanded condition. As shown, the device 100 has a retaining band 60 encircling an upper lift body 20 and lower lift body 40. The upper lift body 20 is at the top of the device and the lower lift body 40 is shown at the bottom of the device. The upper lift body 20, as illustrated, has a lift surface 101 for contacting a vertebrae and the lower lift body 40 has a lift surface 102 for contacting an adjacent vertebrae such that when the device 100 is inserted between vertebrae the lift surfaces 101, 102 can come in contact with the vertebrae abutting the vertebrae in such a fashion as to expand the distance between the vertebrae. As shown, facets or roughened surfaces 103 are provided on the device. These roughened surfaces 103 can be small facets, as shown, for helping to hold and grip the device 100 in position, or alternatively can be further provided with biologically enhancing surfaces to increase the osteoconductivity of the device 100 to enhance bone growth formation.

Figure 2:
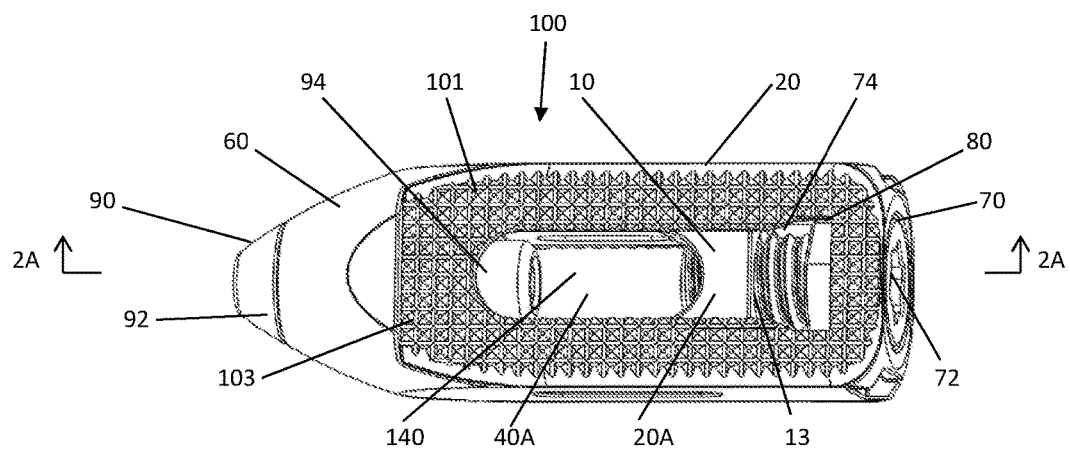
FIG. 2 is a top view taken along lines 2A-2A of FIG. 2 of the expandable implant device of the present invention looking into the implant device in its fully retracted and contracted position.

As shown, the retaining band 60 has a leading end 61. The leading end 61 is the end of the device 100 that is first inserted in through the surgical opening and in position between the pair of vertebrae being spaced in the spine. This leading end 61, as shown, has a slightly bullet or conical shape that facilitates the entry into the spine. A nose portion 90 is shown extending from this leading end 61. At the aft end of the device 100 is shown a threaded fastener, the fester is screw 70. This screw 70 is used for rotating a center body 10 for rotating and moving along the length of the device a center body 10. At the aft end of the device are shown two depressions 64, these depressions 64 help orient and control the position the device 100 when held by an insertion tool. The screw 70 is preferably retained in the device 100 by a retaining clip 80 as illustrated in FIG. 2. It is important to note that the assembly of components is illustrated in an exploded view as shown in FIG. 4.

Figure 4:
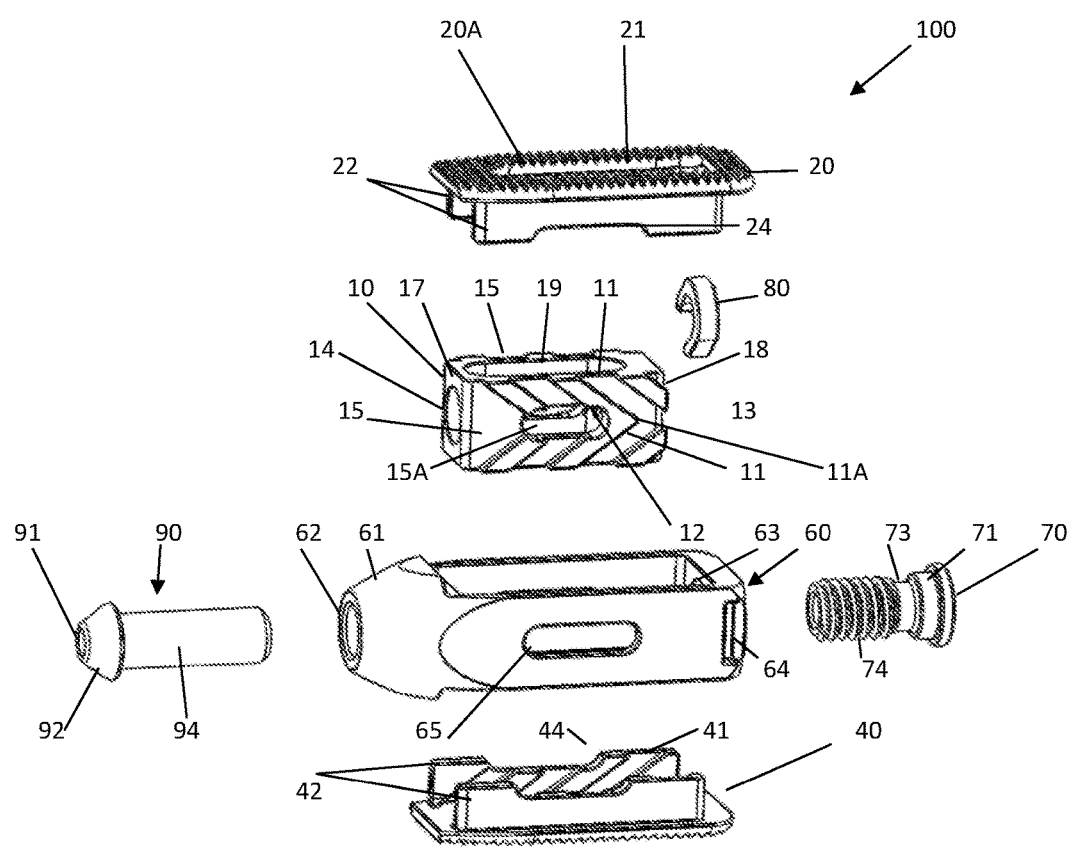
FIG. 4 is an exploded view of the implant device of FIG. 1 showing the various components of the device of the present invention.

With reference to FIG. 4, the retaining band 60 with its leading end 61 and center opening 62 into which nose portion 90 can be inserted. The nose portion 90 is fixed to the retaining band 60 and has a shank 94 which is press fit into the opening 62 as illustrated. An enlarged tapered head 92 at the end of the nose portion 90 that generally provides a uniform contour of the nose portion 90 with the leading tapered end 61 of the retaining band 60. As shown the screw or fastener 70 can be inserted through and held in an opening 63 at the aft end of the device 100. The opening 63 is designed to accept the larger diameter 71 on the shank of the threaded fastener 70. The enlarged screw head is contained in a larger opening 66 concentric to the opening 63 in the retaining band 60. A recess grooved portion 73 is provided onto which a retaining clip 80 can be snapped to hold the threaded fastener 70 to the retaining band 60. The threaded portion 74 of the screw 70 can be inserted into a threaded opening 13 in the center body 10. The threaded opening 13 accepts the threads 74 of the screw 70 and therefore upon rotation of the screw 70 the center body 10 can move relative to the retaining band 60 in a forward or rearward direction towards or away from the leading end 61. As further shown in FIG. 4, an opening 14 is provided, the opening 14 like the opening 62 of the retaining band 60 accepts the shank 94 of the nose portion 90 in such a fashion that the end of the center body 10 is supported on the shank 94 as the center body slides on the shank 94 and is moved fore and aft. As further shown the center body 10 is fundamentally a hollow structure with sides 15 and ends 17, 18. This hollow structure has an opening 19 through the device 100. This opening 19 forms part of a hollow cavity 140 through the device 100. On each side 15 of the center body 10 are shown a plurality of ramps 11 inclined in such a fashion to form chevrons that have an apex 11A at a mid side on each side 15 of the center body 10. These chevrons 11 extend outwardly on an inclination that provides a ramp surface that will enable the upper lift body 20 and lower lift body 40 to slide. As shown, the sides 15 further each have a slotted side opening 15A. These side openings 15A provide access into the device 100 so that bone growth enhancing materials can be added into the device 100 to facilitate new bone growth formation once the device is implanted.

Similarly, as shown on the retaining band 60, a slotted opening 65 is provided on each side of the device 100. These slotted openings 65 are slightly longer than the openings 15A of the center body 10 such that during the movement of the center body 10 relative to the retaining band 60 the slotted openings are maintained in alignment to form through passages. Additionally, the upper lift body 20 is shown with a pair of sides 22. These sides 22 have a recessed portion or cut out 24 as shown. These cut outs 24 are slightly longer than the opening 15A of the center body 10 and as such they also are aligned with the slotted openings such that bone filler material can be added through these lateral openings both on the upper lift body 20 and as shown on the lower lift body 40 having a similar pair of sides 42 with recess portions 44. As shown, both the upper lift body 20 and the lower lift body 40 have complimentary ramp surfaces 21 and 41 respectively. These ramp surfaces 21, 41 are adapted to fit within the channels formed by the ramps 11 on the center body 10. When assembled, the upper 20 and lower 40 bodies fit into the ramp surfaces 11 and in the fully retracted position, the upper lift body 20 and the lower lift body 40 are in close proximity to the apex 11A of the chevron shaped ramp surfaces 11.

With reference to FIG. 2, a top view is shown of the device 100 in the fully contracted position. In this position, a plurality of threads 74 is shown wherein the center body 10 is shifted toward the leading end 61 in the retaining band 60 of the device 100. The center body 10 by being shifted toward the leading end 61 of the retaining band 60 of the device 100 has the shank 94 visibly observable through openings in the top lift body in such a fashion that the center body 10 is fully supported by the shank 94 at one end and the threaded fastener 70 at the other end.

Figure 2A:
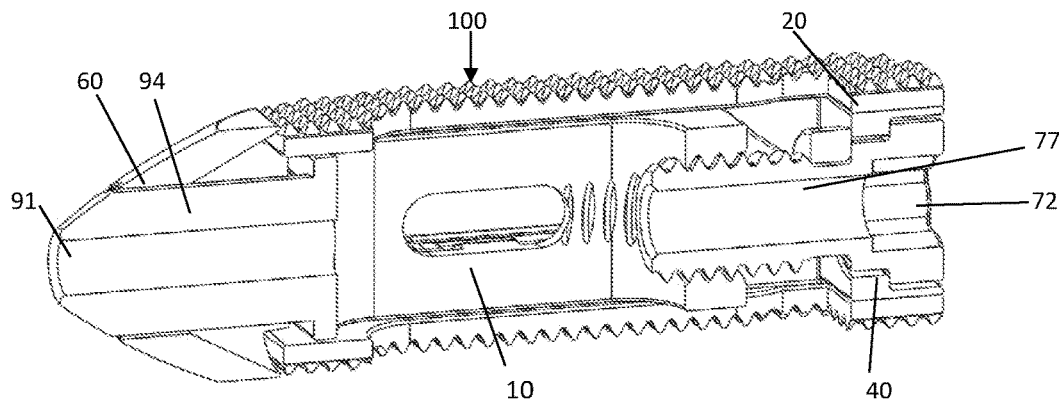
FIG. 2A is a cross sectional view of the expandable implant device of the present invention looking into the implant device in its fully retracted and contracted position taken along lines 2A-2A of FIG. 2.

As further shown in FIG. 2A, a cross sectional view of the contracted unexpanded device 100 shows the nose portion 90 is hollow having an opening 91. Similarly the screw 70 is hollow having an opening 77. These openings allow the device 100 to be guided by a K-wire during the implantation procedure. The end of the screw 70 has a star shaped cavity 72 for inserting a tool to provide rotation.

Figure 3:
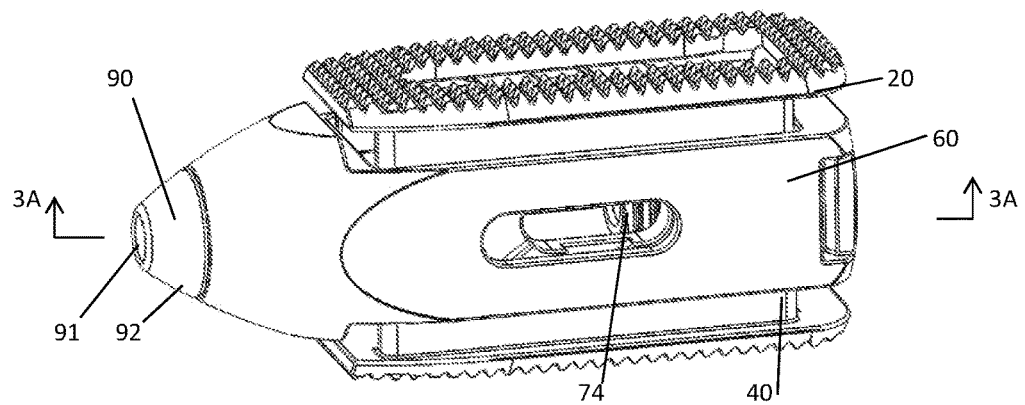
FIG. 3 is a perspective view of the implant device of FIG. 1 shown in the expanded condition.
Figure 3A:
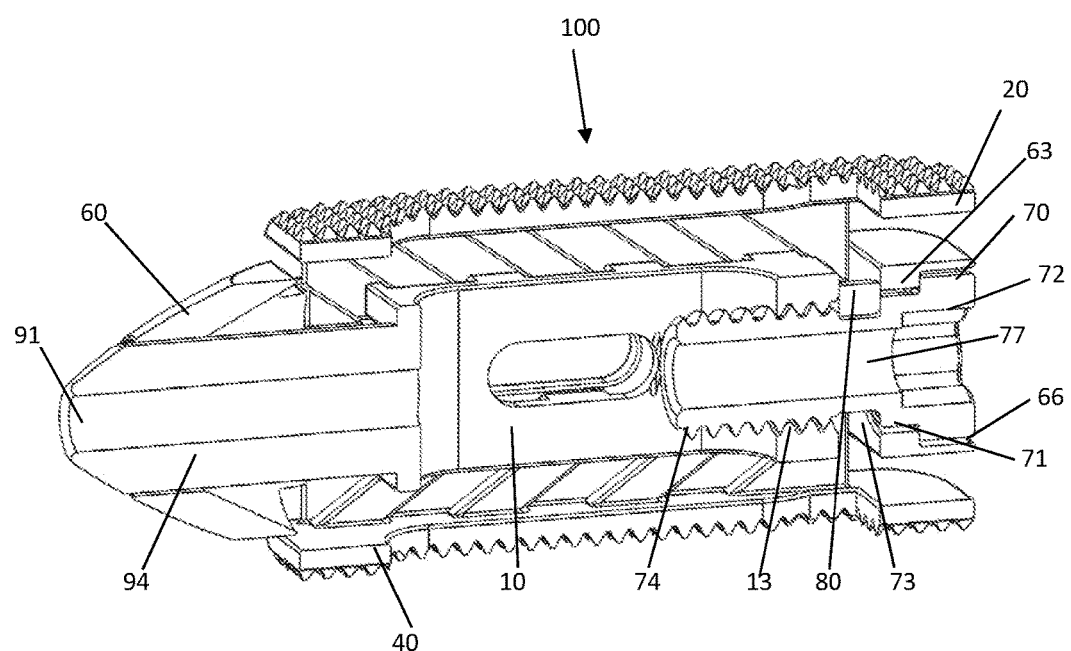
FIG. 3A is a cross sectional view of the implant device of FIG. 1 shown in the expanded condition taken along lines 3A-3A of FIG. 3.

In FIG. 3, as illustrated, the device 100 is shown in an expanded condition. When this occurs, the threads 74 proceed when rotated to extend inward into the center body 10, as best illustrated in FIG. 3A which is a cross sectional view of the expanded device 100.

Figure 5:
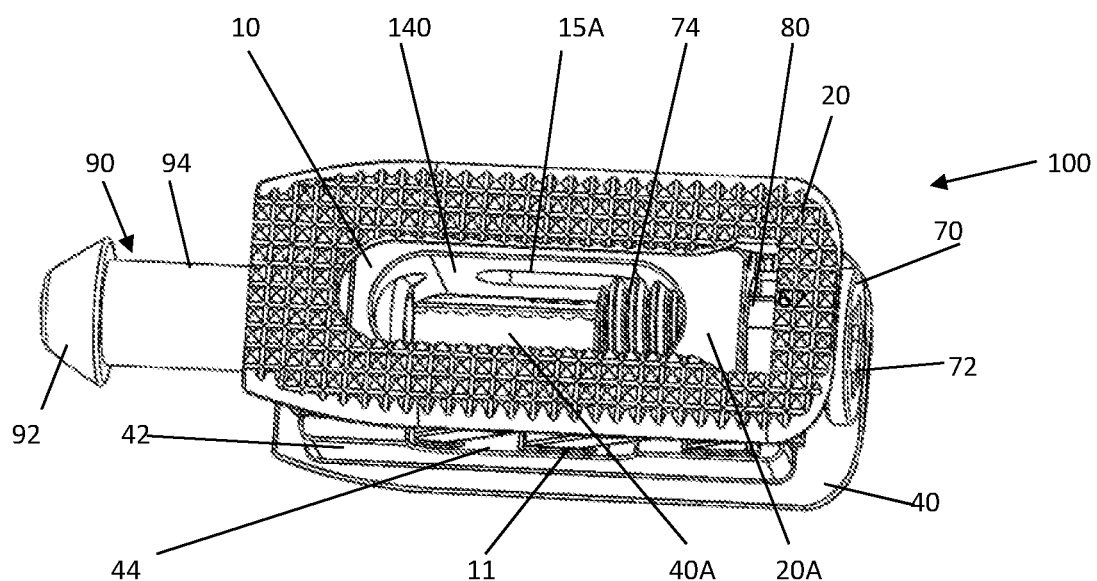
FIG. 5 is a top perspective view looking down on the device wherein the exterior retaining band is removed to show the elements of the device when it is in its fully expanded position.

With reference to FIG. 5, as shown a top perspective view of the device 100 in the fully expanded condition is illustrated. As shown, when the device 100 is expanded the center body 10 moves toward the aft direction and abuts in the fully expanded condition the retaining clip 80 as the device 100 is fully moved as far as it possibly can be to a maximum height condition. As shown the threads 74 are shown clearly exposed into the hollow cavity 140 formed by the center body 10 and only a small portion of the shank 94 is left to retain the center body 10 in a secure and stable condition. It is during this procedure that the ramp surfaces 21, 41 of the upper body 20 and lower body 40 slide along the ramps 11 of the center body 10 outwardly from the apex 11A thereby causing the upper body 20 and lower body 40 to move outwardly increasing the vertical height of the device 100.

As shown in the illustrated first embodiment of FIGS. 1-5, the implant device 100 is substantially an elongated oblong shaped device 100 with straight sides with a leading curved end and a substantially flat trailing end. This device 100 can vary in size having a length of 20 to 40 mm, preferably 26 to 34 mm, and a height of 5 to 15 mm, preferably 8 to 12 mm. In the example, the device 100 is about 9 mm in height. The width of the device is between 8 to 15 mm or 8 to 12 mm, as shown about 9 mm. While the two sides are shown as straight and parallel in their respective lengths, each side could have an outward bowed center increasing the size or surface area. It being understood the complimentary ramp surfaces of the lift bodies 20, 40 would have to be adjusted to accommodate such curvatures.

Figure 7:
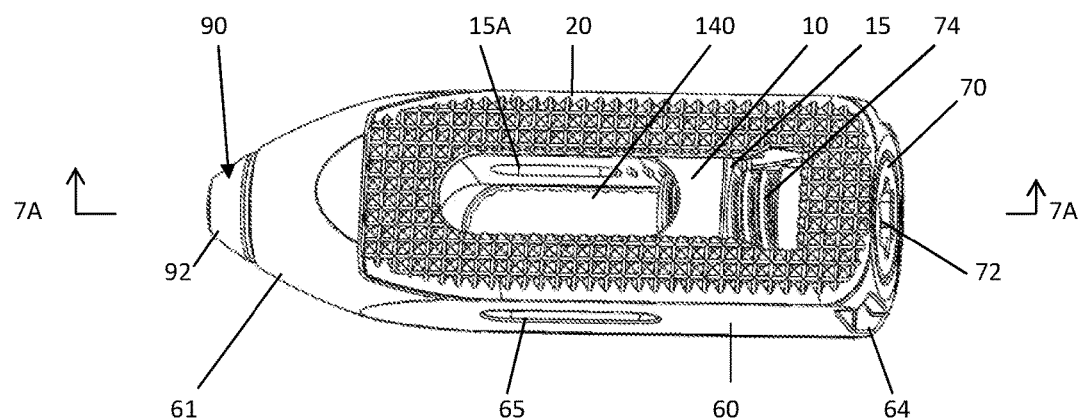
FIG. 7 is a top view of the implant device of FIG. 6 shown in the contracted position.
Figure 8:
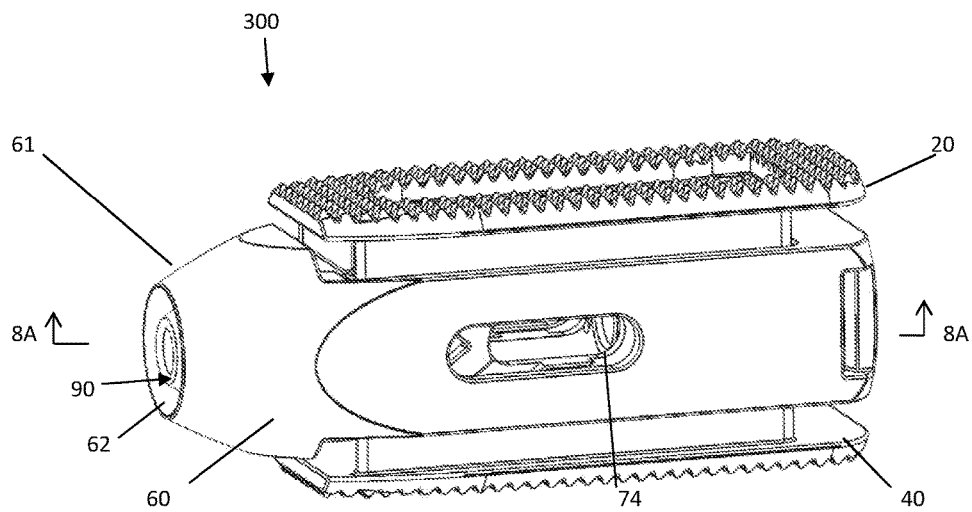
FIG. 8 is a side perspective view of the implant device of FIG. 6 shown in the fully expanded position.
Figure 8A:
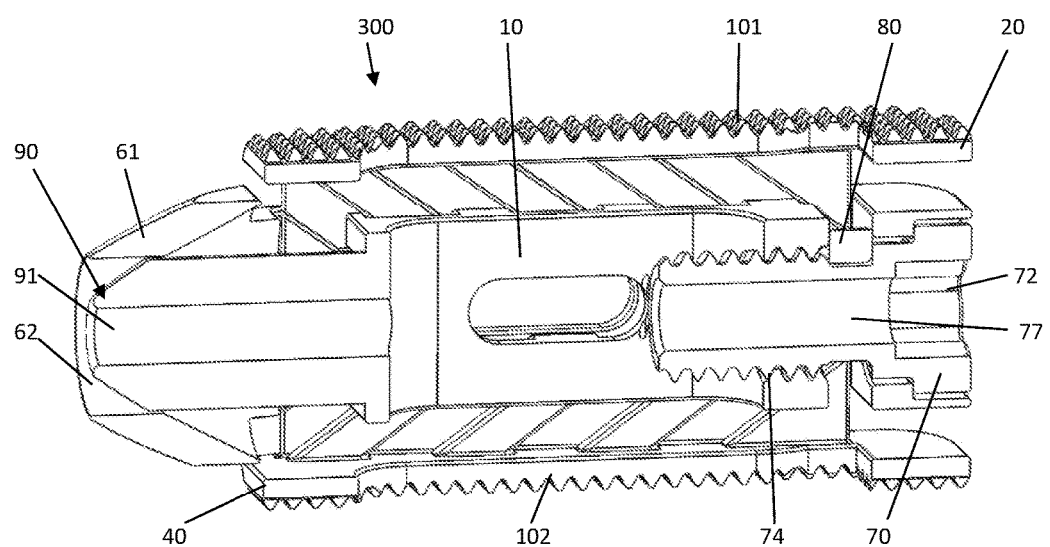
FIG. 8A is a cross sectional view taken along lines 8A-8A of the implant device of FIG. 8 shown in the fully expanded position.
Figure 9:
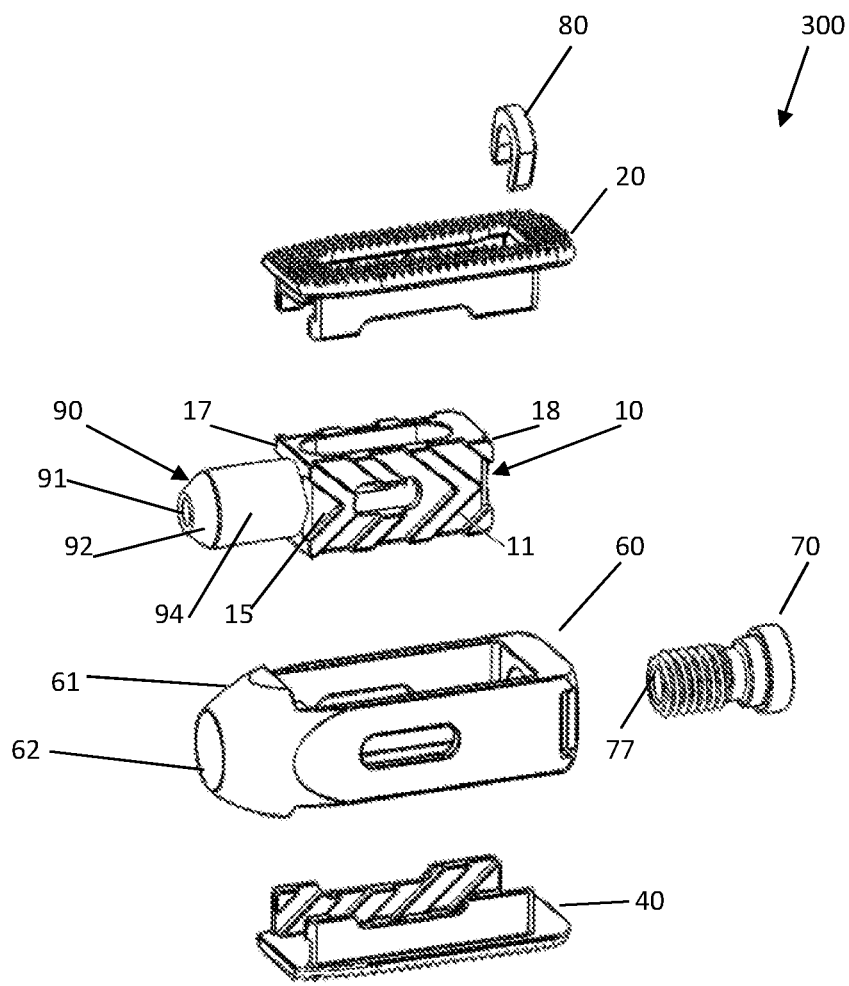
FIG. 9 is an exploded view of the components used in the implant device of FIG. 6.
Figure 9A:
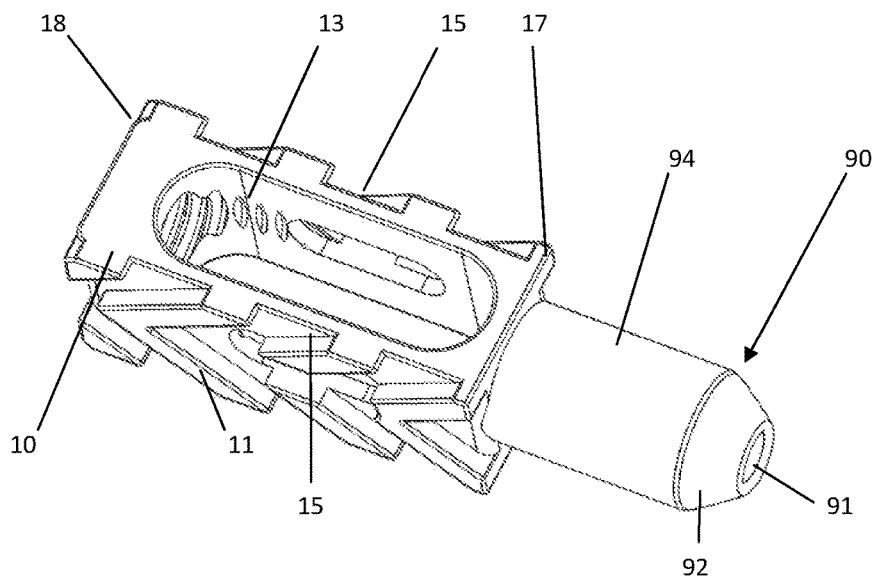
FIG. 9A is a perspective view of the center body of the second alternative embodiment.

With reference to FIGS. 6-9, an alternative second embodiment of the present invention expandable implant device 300 is illustrated. This implant device 300 has all the components of the previous first embodiment as illustrated in the exploded view of FIG. 9 showing the various components employed. This device 300 similarly has an upper lift body 20 a lower lift body 40, a retaining band 60, a center body 10 and a threaded fastener or screw 70 and retaining clip 80. All of these components are as previously described having similar ramps 11 on the center body 10 along each side 15, but at the leading end of the center body 10, the nose portion 90 has been affixed or is integral to the leading end 17 of the center body 10. In this fashion, the nose portion 90 is now moveable along with the movement of the center body 10, as before, the nose portion 90 is hollow having the opening 91 as is the screw 70 with its opening 77. Accordingly, when the center body 10 is pulled toward the aft direction by the rotation of the threaded fastener 70, the nose portion 90 with its reduced sized head 92 and shank 94 moves with the center body 10. In this fashion, the entire nose portion 90 is adapted to slide within the opening 62 at the leading end 61 of the retaining band 60. This creates a support for the center body 10 as previously discussed by the employment of the shank 94 as it is pulled inside the retaining band 60. The shank 94 is fully supported by the opening 62 such that the device 300 is stabilized at both the forward end by the shank 94 and by the threaded fastener 70 at the aft end. All other functions of the device are very similar, the advantages of this alternative embodiment is that the head 92 of the nose portion 90 which can have a length over 2 mm can be fully retracted into the opening 62 by the movement of the center body 10 toward the aft direction when the device 300 is expanded. This allows the surgeon to use an upper lift body 20 and lower lift body 40 that is slightly longer because the nose portion 90 by being retracted is withdrawn and, therefore, a longer device 300 can be employed allowing for additional support of the vertebrae during implantation.

Accordingly, the nose portion 90 having a tapered end 92 has no support for the vertebrae and therefore, ideally, the tapered end 92 of nose portion 90 which greatly facilitates entry of the device 300 during insertion, can be retracted after insertion so that the overall length of the implanted device 300 is reduced while the supporting portion of the upper lift body 20 and lower lift body 40 can be the same or increased slightly due to the reduction in length created by retracting end 92.

Figure 6:
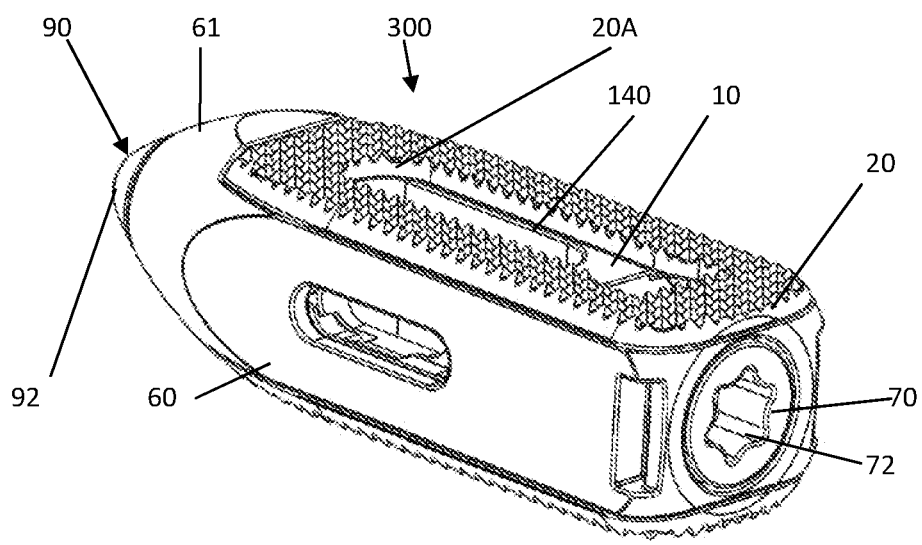
FIG. 6 is a perspective view of a second alternative embodiment expanded implant device of the present invention.
Figure 6A:
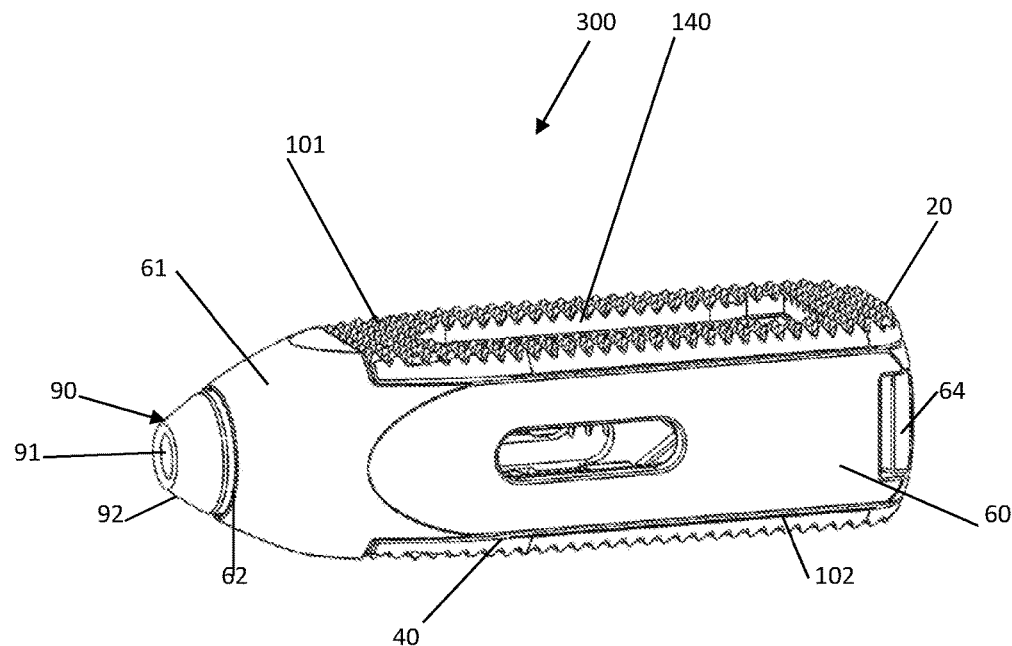
FIG. 6A is a side perspective view of the implant device shown in its fully contracted position.

FIG. 6 shows a perspective view of the device 200 with the nose end 92 shown in the fully extended position. FIG. 6A is a side view again showing the nose extending slightly outwardly from the leading portion 61 of the retaining band 60.

Figure 7A:
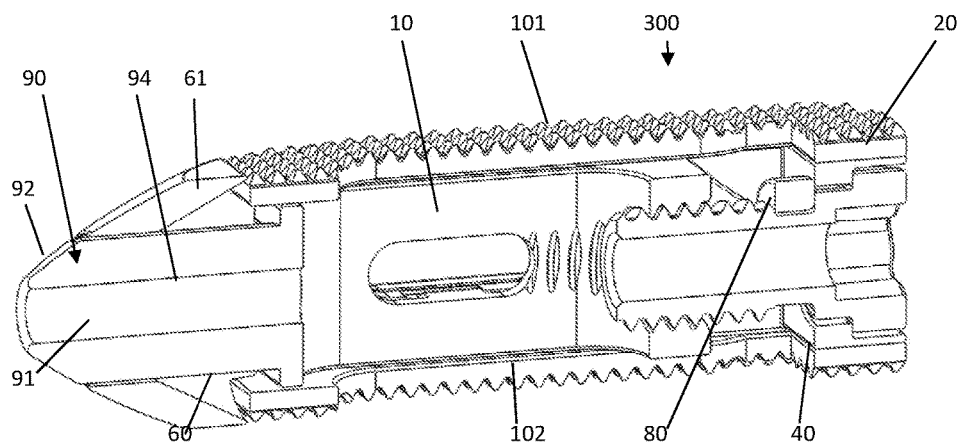
FIG. 7A is a cross sectional view of the implant device of FIG. 6 shown in the contracted position taken along lines 7A-7A of FIG. 7.

FIG. 7 is a top showing the fastener 70 with a few threads 74 only partially extending into the center body 10 through the threaded end 13 showing that there are a large number of threads 74 available to move the center body 10 in an aft direction. Due to the large diameter of the threads 74 the threaded opening 13 on the center body 10 shows thread portions in the sides 15, this is best seen in FIG. 7A which is a cross sectional view of the device 300.

Figure 10:
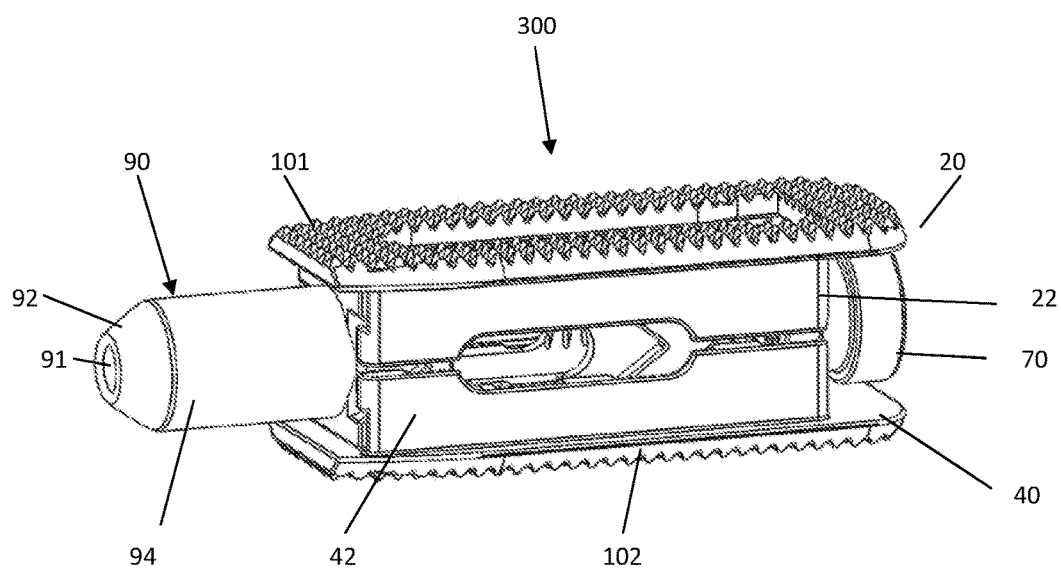
FIG. 10 is a side perspective view of the implant device of FIG. 6 wherein the outer retaining band has been removed showing the implant device in its contracted position.
Figure 11:
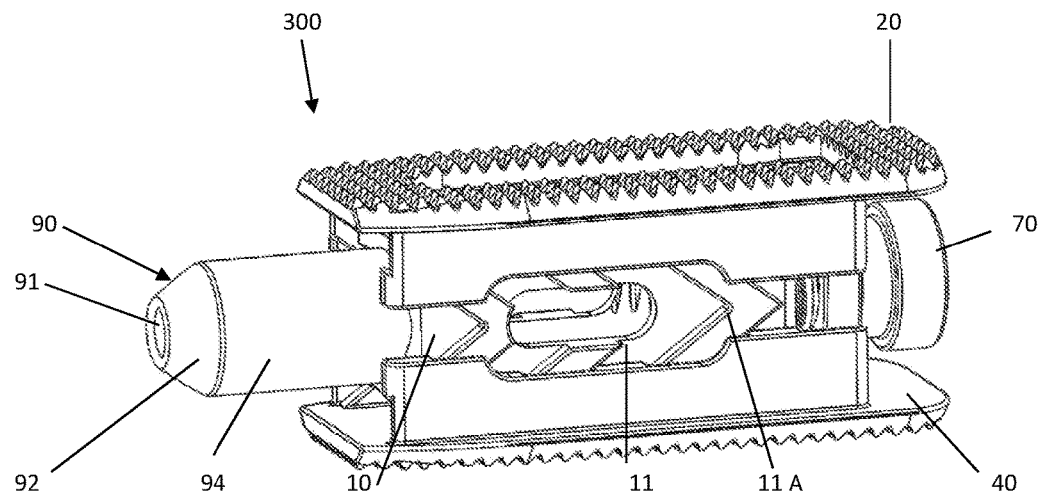
FIG. 11 is a side perspective view of the implant device of FIG. 6 wherein the outer retaining band has been removed showing the implant device in a mid expanded position.
Figure 12:
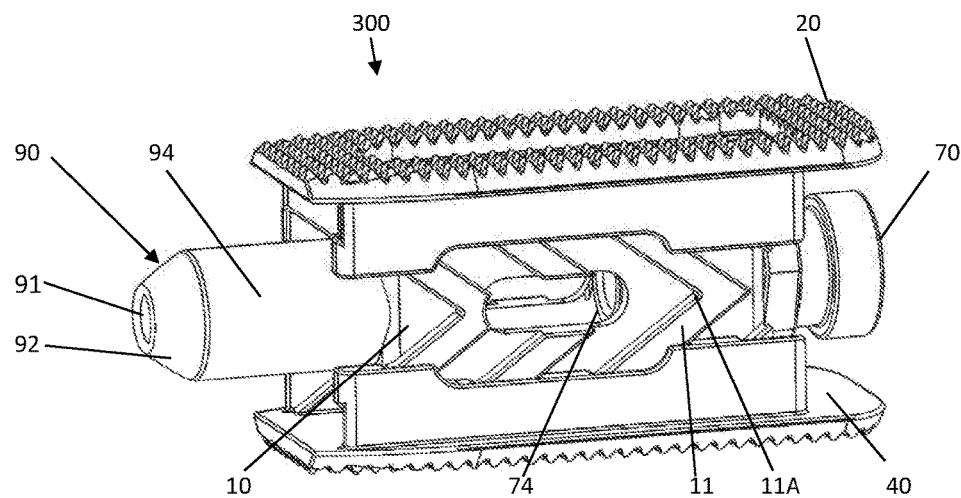
FIG. 12 is a side perspective view of the implant device of FIG. 6 wherein the outer retaining band has been removed showing the implant device in its fully expanded condition.
Figure 13A:
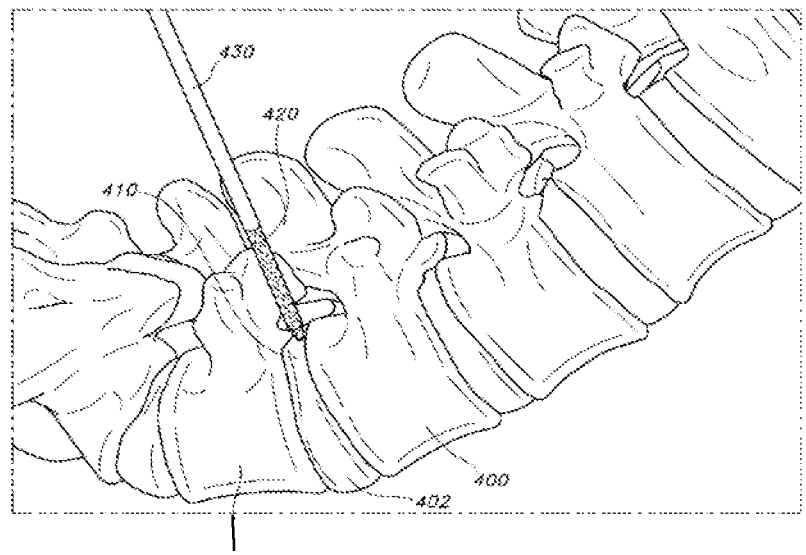
FIGS. 13A-13E are views of an exemplary method of using the device in a vertebrae repair showing that portion of the spine.
Figure 13B:
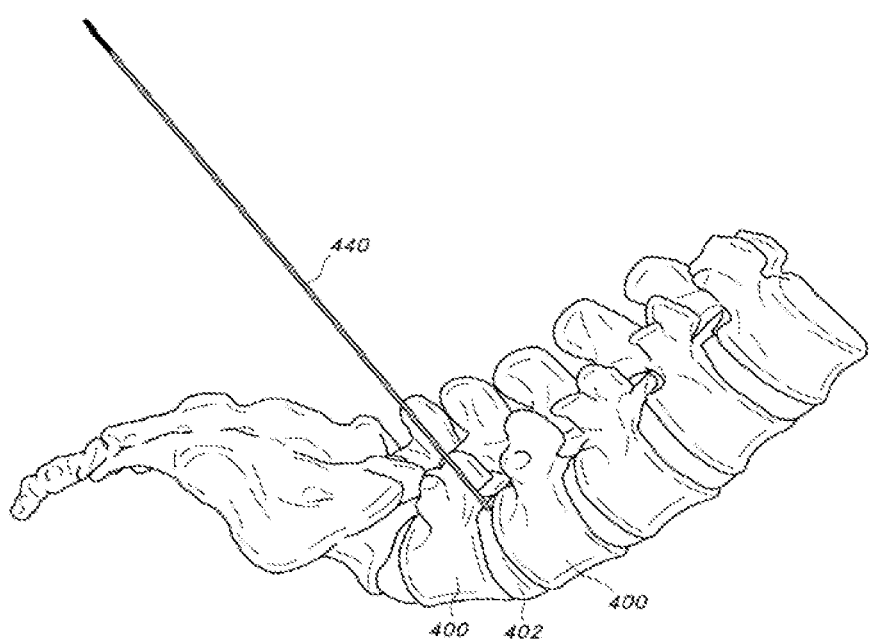
Figure 13C:
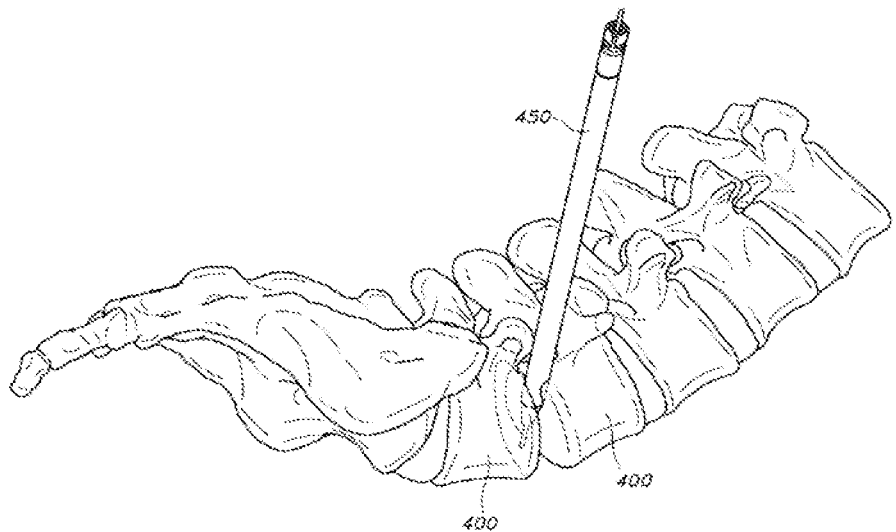
Figure 13D:
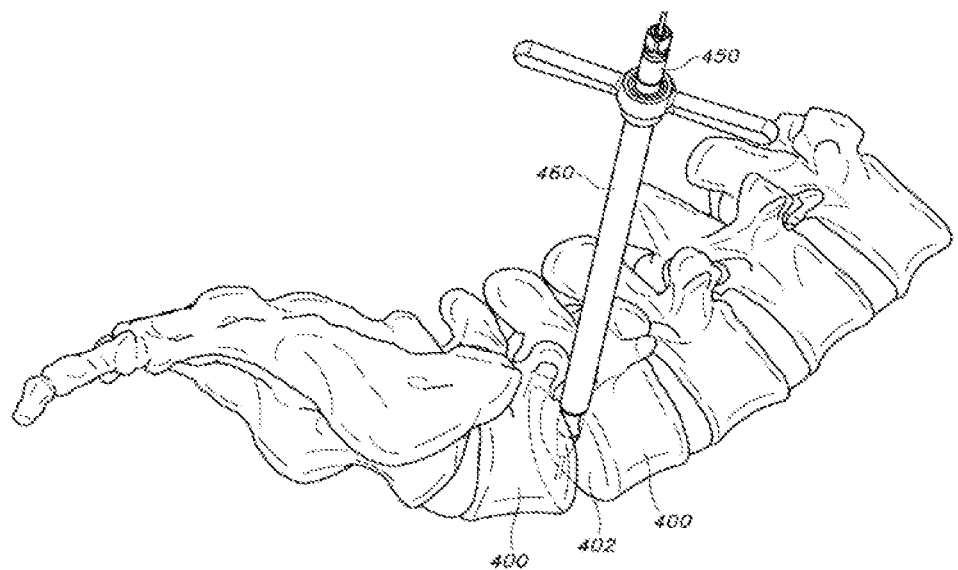
Figure 13E:
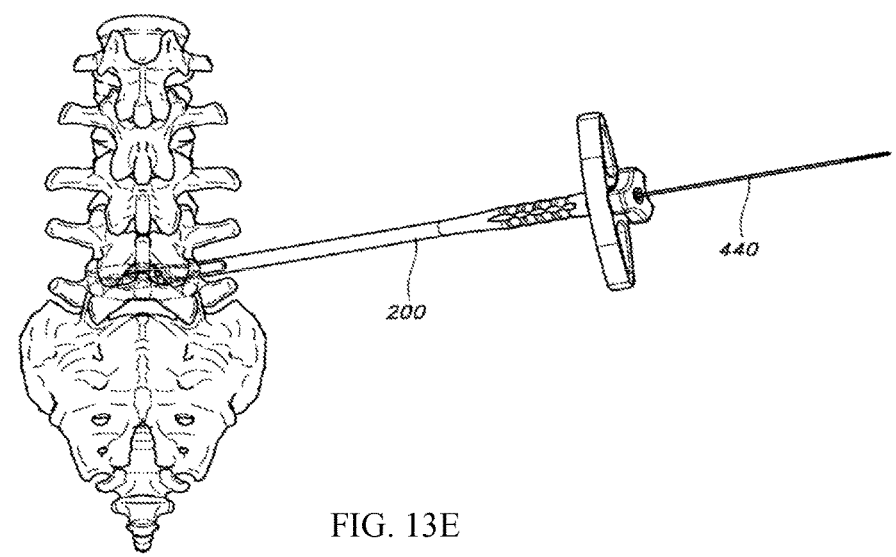

FIG. 8 shows that the device 300 in an expanded condition with the upper body 20 and lower body 40 expanded and the nose portion 90 shown withdrawn into the opening 62 at the leading end 61 of the retaining band 60. As shown through the slotted openings in the side of the retaining band 60 and center opening, the threads 74 are shown extending into the center body 10. This is most easily seen in the cross sectional view 8A as the center body 10 is moved to the aft end of the device 300. This is also illustrated in FIGS. 10, 11 and 12 wherein the retaining band 60 has been removed to better illustrate the device 300. In this embodiment it is understood that the nose portion shank 94 moves directionally with the movement of the center body 10. As illustrated in FIG. 10, when the upper lift body 20 and lower lift body 40 are contracted as previously discussed, a minimum height is achieved. When this minimum height is achieved, the device 300 is optimally set for insertion between the vertebrae. Once the device 300 is inserted between the vertebrae, rotation of the screw 70 can be achieved by an insertion tool adapted to rotate the star shape opening 72 as discussed later. This rotation of the screw 70 will cause the lift bodies 20, 40 to ride along the ramp surfaces 11 extending outwardly increasing the height. FIG. 11 shows the device partially expanded and FIG. 12 shows it fully expanded.

It is important to note that the retaining band 60 provides the ability to hold the sides 22, 42 sandwiched between the center body 10 and the retaining band 60 so that the ramped surfaces 21, 41 stay actively engaged throughout the lifting procedure and cannot be moved off the ramps 11. Alternatively, although not shown, the ramps 11 could be provided on the retaining band 60 and the center body 10 could be provided having smooth sides and the complimentary ramp surfaces positioned on the external surface of the sides 22, 42.

With reference to FIGS. 1 and 6, the expandable implant device 100, 300 made according to the present invention are illustrated. As shown, the implant devices 100, 300 is in the fully retracted unexpanded condition. As shown, the device 100 has an upper body 20, a lower body 40 and a retaining band 60 encircling both the upper and lower lift bodies. In one embodiment, the upper and lower bodies can be made of a plastic or synthetic material. Preferably, in this embodiment, this material is PEEK (PolyEtherEtherKetone) although alternative materials can be used for either of the upper or lower body. The top outer surface 101 of the upper body 20 and the bottom outer surface 102 of the lower body 40 are provided with a plurality of facets or ridges 103 or roughened surfaces. These surfaces 101, 102 will contact the vertebrae when installed and expanded and provide a gripping surface to which the implant is securely held when expanded between the two spaced vertebrae as discussed.

In both devices 100, 300 an important aspect is the sides 22 of the upper lift body 20 and sides 42 of the lower lift body 40 extend lengthwise to approximate the size of the opening in the retaining band 60 into which they extend inwardly. This insures the sides have limited movement lengthwise being held closely inside the leading end and trailing end of the retaining band 60. This forces the lift bodies 20, 40 to move on the ramps 11 as the center body 10 is moved lengthwise. As shown, even in the fully expanded condition, the sides 22, 42 are extending inwardly sufficiently so they are always held in the retaining band 60.

As shown, the expandable implant devices 100, 300 in the illustrations are elongated oblong oval shaped devices with straight sides with leading curved end and a generally substantially flat trailing end. The retracted unexpanded device can vary in size having a length of 20 to 40 mm, preferably 26 to 34 mm and a height of 5 to 15 mm, preferably 8 to 12 mm, in the example about 9 mm. The width of the device is between 8 to 15 mm or 8 to 12 mm, as shown 9 mm. While the two sides are illustrated as straight and parallel in their respective lengths, each of the sides could have an outwardly bowed center increasing the size and surface area. Alternatively, the two sides can take on a curved configuration of a banana shape or parallel crescents along the length to more optimally fit the space between the vertebrae. All these shapes can employ the inventive features of the device 100 or 300.

It is important to note in FIGS. 1 and 6, that the space between the upper lift body 20 and lower lift body 40 between the interior surfaces form a hollow cavity 140 into which bone growth material can be inserted either on a preassembly into the device or preferably after the expandable implant device 100, 300 has been inserted into the spine. As shown in FIGS. 1 and 6, the implant device 100, 300 upper lift body 20 and lower lift body 40 has an oval elongated opening 20A, 40A at the top and bottom. This opening 20A, 40A provides easy packing of the bone growth material on preassembly, however, once assembled these areas are blocked by the vertebrae. Accordingly, when the insertion tool is removed, the cavity 140, as shown in FIG. 7 in the expanded condition, is enlarged greatly resulting in the volumetric space being increased dramatically, by the expansion of the implant device 100, 300. When this occurs, additional bone growth material or all the bone growth material can be inserted when the insertion tool 200 is removed. Once the insertion tool 200 is removed, the bone growth material (not shown) can fully pack the implant device 100, 300 through the slotted openings 64 and is in direct contact with the surface of the vertebrae through the oval openings of the cavity 140 at the top surface or end 101 and bottom surface or end 102. Once the device 100, 300 is inserted and the insertion tool 200 is withdrawn through the opening, the manipulation is complete. The outward movement is facilitated by the ramp surface 11, typically inclined than 30 degrees off vertical, preferably 45 degrees. The inward movement is blocked by the fastener 70 so compressive forces pushing the bodies inwardly are stopped.

With reference to the insertion tool 200, it is noted that the insertion tool 200 can have a hollow hole 500 extending all the way through the shaft 204 from one end to the other. This hollow hole 500 provides a means or access for which a K wire can be slipped through the insertion tool 200 and the implant device 100, 300. During the surgical procedure, it is preferable that the insertion tool 200 is fully inserted into the implant device 100, 300 and that a pre-inserted K wire that has been placed in the location where the implant device 100, 300 is to be directed to its preferred position in between the vertebrae in such a fashion that as the surgeon inserts the implant device 100, 300 with the insertion tool 200 securely holding the device 100, 300, he may then be guided to the proper location by use of the K wire. To further this procedure, applicants have provided FIGS. 13A-13E showing some of the actual insertion steps of an implant device insertion.

As illustrated in FIG. 1 or FIG. 6, the expandable implant device 100, 300 has two opposing longitudinal extending outer surfaces with gripping facets 103 each defining ridged top or bottom surfaces or ends 101, 102. The ridged gripping surfaces or ends 101, 102 are meant to assist with the implant's ability to grip the adjacent bone structure. In one aspect, the ridges can be angled in order to assist in preventing the implant from backing out.

Sometimes, it is beneficial to have the means with which to promote bone growth and/or fusion. In one aspect, the implant device 100, 300 further defines an implant cavity 140 in communication with the implant aperture and substantially open to at least one, or both, of the top or bottom gripping surfaces or ends 101, 102. In this aspect, bone graft material or bone cement can be introduced into the implant cavity 140. The bone graft material can be, for example, autologous bone, allograft bone, bone substitute, osteoinductive agents, and the like.

The implant 100, 300 itself comprises a biocompatible material, capable of being inserted into the body. In one aspect, the bio-compatible material for the upper and lower body is selected from the group consisting of PolyEtherEtherKetone, ceramic, allograft bone, and PolyEtherEtherKetone with $BaSO_4$. Other biocompatible materials are also contemplated. The retaining band is preferably made of titanium. Alternatively, the entire device can be made of metal, preferably stainless steel or titanium or a mixture of components using these two metals or eve in combination with plastic components. To facilitate a better understanding of how the present inventive expandable implant can be used, exemplary methods of the procedure are provided. These methods are as described in U.S. Pat. No. 8,496,709 entitled "Spinal Implant" granted on Jul. 30, 2013 and commonly owned by assignee Amendia, Inc. of Atlanta, Ga.; the contents of which are incorporated herein by reference in its entirety.

Also presented herein is an exemplary percutaneous fusion method to correct disc compression. The method, in one aspect illustrated in FIGS. 13A-13E, comprises making a posterolateral incision to access the desired spinal motion segment; determining a target level of the disc space 402 between adjacent vertebral bodies 400 for implantation of an implant; locating a path to the disc space at the target level; inserting a guide wire 440 to maintain a path to the disc space 402; sliding the spinal implant along the guide wire 440 to position it into the disc space at the desired position; removing the guide wire; and fixating at least a portion of the desired spinal motion segment.

This first step comprises making a posterolateral incision to access the desired spinal motion segment. In one aspect, the initial access point can be made through Kambin's Triangle 410. Kambin's Triangle, as those skilled in the art will appreciate, is the site of surgical access for posterolateral endoscopic discectomy. It is defined as a right triangle over the dorsolateral disc. The hypotenuse is the exiting nerve, the base (width) is the superior border of the caudal vertebra, and the height is the traversing nerve root.

The method also comprises determining the target level of the disc space between adjacent vertebral bodies 400. Once the target level is established, the method comprises locating a path to the disc space at the target level. This can be accomplished, for example, using a nerve monitoring probe 420 with a transfer sleeve 430. The nerve monitoring probe can measure the proximity of the exiting nerve root. Once measured, in an exemplified aspect, the probe 420 can then be removed, leaving the transfer sleeve 430 in place. In one aspect, the nerve monitoring probe comprises an EMG Navigation system, comprising a blunt-tipped monopolar probe and an exchange cannula.

The method also comprises inserting a guide wire through the transfer sleeve to maintain a path to the disc space. In one aspect, the guide wire 440 can be a Kirschner wire or k-wire. After insertion of the guide wire, one aspect of the method comprises removing the transfer sleeve and placing a dilator 450 over the guide wire. The dilator 450 can be driven into the disc space 402 to distract the vertebral bodies 400.

In one aspect, the next step comprises positioning an access portal 460 into the disc space. For instance, in one exemplified aspect, the surgeon can slide the access portal 460 over the dilator and use an impact sleeve with a mallet to lodge the portal into the disc space. The dilator and guide wire can then be removed, leaving the access portal in place.

In a further aspect, the method can comprise performing a discectomy and decorticating the vertebral endplates. In an exemplified aspect, a drill can be used to access the nucleus and prepare the area for other discectomy instruments. For example, and not meant to be limiting, a disc shaper, can be used for endplate preparation. The surgeon may elect to remove some of the loose disc material at this point. As such, a pituitary rongeur can be used. In another aspect, a disc cutter can be used to accomplish a thorough discectomy. After which, the pituitary rongeur can be used again to remove remaining disc remnants.

In one aspect, a bone graft (not shown) can then to be introduced. As one skilled in the art can appreciate, this can be accomplished through the portal using a tube and plunger system. In one aspect, the bone graft is a sentinel bone graft. The surgeon can then re-introduce the guide wire 440 and remove the access portal 460.

With input from pre-surgical radiographic film, the next step can comprise determining the height of an adjacent level healthy disc to assist with the selection of the proper amount implant. The size of the implant 100 or 300 can be easily determined avoiding the need to be confirmed with a paddle trial or a solid body trial. In the U.S. Pat. No. 8,496,709; to do so, the surgeon had to first insert the trial implant along a path, guided by the guide wire. An insertion tool 200, as described herein above, had been used. Once inserted, if the selected trial implant cannot be rotated into an erect position, the surgeon could then step down to a smaller size. Alternately, if the selected trail can be rotated into an erect position without much frictional resistance, the surgeon could choose the next larger size. Several iterations were necessary to achieve the correctly sized implant. In the present invention using the expandable implant, this procedure is unnecessary, saving much time.

As described herein above, in one aspect, the implant 100, 300 comprises an implant cavity 140. As such, the method comprises, after determining the appropriate implant height, loading graft material into the implant cavity and connecting the implant to the insertion tool and following the guide wire to insert the implant. Imaging technology can be used to verify the correct location of the implant. In one aspect, fluorographic imaging can be used to watch radiographic markers in order to determine the correct location of the implant. In one aspect, as determined by the surgeon, when the images show the radiographic markers evenly placed on each side of the spinous processes, the implant is placed properly. Once the implant is placed properly, the surgeon can then rotate the insertion tool thereby expanding the implant device to the desired height and release it from the insertion tool 200.

As illustrated, as the upper body 20 and lower body 40 move relative to the retaining band 60, the movement outwardly is controlled and maintained parallel relationship to the length of the device avoiding or preventing any angular tilting or cocking. This insures the expansion of the bone contacting outer top or bottom surfaces or ends 101, 102 is accomplished uniformly, evenly and simultaneously. While the direction or path of the movement is clearly perpendicular to the length of the device 100, 300.

Figure 14:
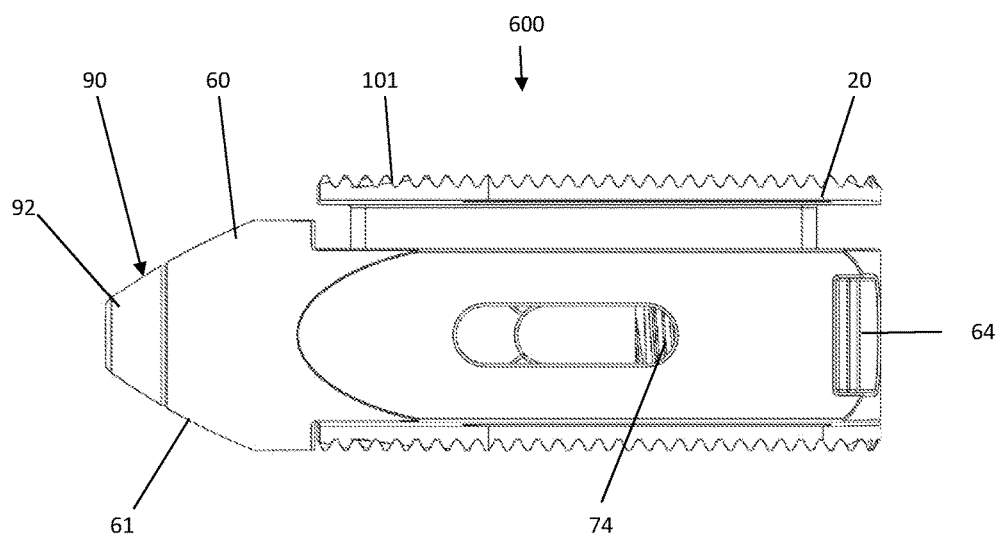
FIG. 14 is a side view of a third alternative embodiment having one lift body moveable.

With reference to FIG. 14, a side view of a third embodiment device 600 of the present invention is shown. The device 600 is virtually identical to the devices 100 and 300 with the important distinction that the device 600 has only one lift body 30 moveably driven by the center body 10. In this embodiment, the opposite end 102 is fixed to or integral with the retaining band 60. As shown, the device is generally symmetrical in its fully retracted condition and as such the one lift body 20 can be oriented so device 600 has the upper or top side or end 101 will move when the lift body 20 is oriented on top or if the device 600 is flipped over, the lower or bottom side will expand as the lift body 20 moves and the top is fixed. In this embodiment, the plurality of ramps 11 on the center body 10 can extend in an inclined straight line the full length of the sides and the complimentary ramp surfaces on the one moveable lift body 20 will be driven as previously described by the center body 10 linear movement from a retracted forward position to the expanded height aft position. As in the previous first and second embodiments, rotation of the screw 70 insures the movement is achieved virtually identical to the two moveable lift bodies albeit in a single upward or a downward direction to space the adjacent vertebrae by the abutting ends 101, 102. In this embodiment, only one lift body 20 is needed making the device 600 slightly simpler in design. It is understood all the features of the nose portion 90 whether fixed as in the first embodiment device 100 or moveably retractable as in the device 300 are usable with this one lift body device 600. Similarly, all the materials contemplated for the device 600 are the same as those previously described for the device 100, 300.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An expandable implant device for insertion between two vertebrae, the device comprising:
   one or more lift bodies;
   a center body retractably moveable relative to a length of the device, wherein the center body has a plurality of sloped ramps along opposing longitudinal extending sides and one or more lift bodies each have a plurality of complimentary sloped surfaces on sides adjacent to opposing sides of the center body wherein lengthwise movement of the center body of the device moves the one or more lift bodies inward or outward relative to the center body, causing an expansion or retraction of height of the device;

an exterior retaining band encircling the sides of the one or more lift bodies, the retaining band having a leading end having an opening;

a threaded fastener having a rotatable fastener head retained to a distal trailing end of the retaining band and a threaded shank attached to a threaded opening at an end of the center body, wherein rotation of the rotatable fastener moves the center body relative to the retaining band causing the one or more lift bodies to raise or lower, the threaded fastener having a center opening for passing a guide wire through the device; and a nose portion at the leading end of the retaining band, the nose portion having the opening of the leading end of the retaining band wherein the opening of the nose portion is configured to pass a guide wire extending through the center body and center opening of the threaded fastener through the device during implantation of the device, and wherein the sloped ramps are inclined directionally outward toward a leading end of the retaining band and rotation of the fastener draws the center body toward the trailing end as the one or more lift bodies move apart increasing the height of the device wherein the one or more lift bodies include an upper lift body and a lower lift body and the sloped ramps of the center body are formed in the shape of a chevron, the chevrons having an apex at a midline of the center body, the apex directionally positioned closer to a trailing end and as the center body moves aft towards the trailing end, the complimentary surfaces of the lift bodies ride along the sloped ramps moving the lift bodies increasing the height of the device, wherein upon movement of the center body the lift bodies on expansion move relative to the nose portion and when the one or more lift bodies are retracted to a low height contracted position the one or more lift bodies are retracted at least partially into the retaining band adjacent to and behind the nose portion.

2. The device of claim 1 wherein the nose portion has a tapered head with a shank filling the opening of the nose portion of the leading end of the retaining band.

3. The device of claim 2 wherein the nose portion has a central passageway extending along the shank through the tapered head to pass a guide wire during implantation of the device.

4. The device of claim 3 wherein the tapered head of the nose portion is conical or bullet shaped.

5. The device of claim 4 wherein the shank is fixed to the center body and upon movement of the center body, the nose portion moves with the center body.

6. The device of claim 5 wherein the nose portion is fully extended relative to the leading end of the retaining band when the one or more lift bodies are retracted to a low height contracted position and is retracted at least partially into the leading end opening when the one or more lift bodies are fully expanded to a maximum height of the device.

7. The device of claim 3 wherein the shank of the nose portion slip fits into an opening of the center body and the center body slides along the shank as it moves while the tapered head of the nose portion is fixed to the opening of the retaining band, thereby fixing the nose portion to the retaining band.

8. The device of claim 1 wherein the one or more lift bodies have ends, the ends each have an elongated opening extending from a respective one or more lift bodies.

9. The device of claim 1 wherein the center body is formed as a hollow structure with sides forming an elongated opening communicating with the openings of the one or more lift bodies.

10. The device of claim 1 wherein the center body has a pair of side openings, and the retaining band has a complimentary set of side openings, one opening being at least partially aligned with each opening in the side of the center body.

11. The device of claim 1 wherein each one or more lift body has a recessed cut out portion on each side, the recessed cut out portions being aligned to form a lateral passageway open through the side openings in the center body, the cut out portions of the one or more lift bodies and the side openings of the retaining band.

12. The device of claim 1 wherein the center body is a hollow oblong or rectangular structure open at a top and a bottom.

13. The device of claim 12 wherein the retaining band is a hollow band, and the sides of the one or more lift bodies are held between the sides of the center body and the retaining band along the length of the device.

14. The device of claim 1 wherein each of the one or more lift bodies has an end for abutting a vertebra.

15. The device of claim 14 wherein each end has an elongated opening.

16. The device of claim 15 wherein each end has a grip surface for abutting the vertebrae.

17. The device of claim 1 wherein the one or more lift bodies and center body are made of metal.

18. The device of claim 1 is made of stainless steel or titanium or plastic or any combination thereof.

19. The device of claim 1 further comprises a clip to hold the fastener to the retaining band.

* * * * *